United States Patent
Weichert et al.

(10) Patent No.: US 9,925,283 B2
(45) Date of Patent: Mar. 27, 2018

(54) ALKYLPHOSPHOCHOLINE ANALOGS FOR MULTIPLE MYELOMA IMAGING AND THERAPY

(71) Applicant: Wisconsin Alumni Research Foundation, Madison, WI (US)

(72) Inventors: Jamey Paul Weichert, Fitchburg, WI (US); Chorom Pak, Madison, WI (US); Benjamin Titz, Madison, WI (US); Fotis Asimakopoulos, Madison, WI (US); Roberta Marino, Cordova, TN (US); Mario Otto, Fitchburg, WI (US); Kevin R. Kozak, Janesville, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/095,641

(22) Filed: Apr. 11, 2016

(65) Prior Publication Data

US 2016/0296646 A1 Oct. 13, 2016

Related U.S. Application Data

(60) Provisional application No. 62/145,732, filed on Apr. 10, 2015.

(51) Int. Cl.
| | | |
|---|---|---|
| *A61K 51/04* | (2006.01) | |
| *G01N 33/60* | (2006.01) | |
| *G01N 33/574* | (2006.01) | |
| *G01N 33/58* | (2006.01) | |

(52) U.S. Cl.
CPC ... *A61K 51/0489* (2013.01); *G01N 33/57407* (2013.01); *G01N 33/582* (2013.01); *G01N 33/60* (2013.01)

(58) Field of Classification Search
CPC .......... A61K 51/00; A61K 49/00; C07F 13/00
See application file for complete search history.

(56) References Cited

U.S. PATENT DOCUMENTS

| | | | |
|---|---|---|---|
| 2010/0284929 A1 | 11/2010 | Pinchuk et al. | |
| 2014/0030187 A1 | 1/2014 | Weichert et al. | |

OTHER PUBLICATIONS

Cellectar Biosciences, Inc., Form 10-K Annual Report, Mar. 19, 2014, pp. 3-11, SEC Edgar Online, Washington, D.C.
Cellectar Biosciences, Cellectar Biosciences Announces Acceptance of Investigational New Drug Application to Evaluate I-131-CLR1404 in Clinical Trials in Relapsed or Refractory Multiple Myeloma, Sep. 14, 2014, pp. 1-2, Globe Newswire (Press Release), Madison, Wisconsin.
Cellectar Biosciences, Cellectar Biosciences Files Investigational New Drug Application to Evaluate I-131-CLR1404 in Clinical Trials in Relapsed or Refractory Multiple Myeloma, Aug. 11, 2014, pp. 1-2, Globe Newswire (Press Release), Madison, Wisconsin.
Cellectar Biosciences, Cellectar Biosciences Granted Orphan Designation for I-131-CLR1404 for the treatment of Multiple Myeloma, Dec. 4, 2014, pp. 1-2, Globe Newswire (Press Release), Madison, Wisconsin.

*Primary Examiner* — Jake M Vu
*Assistant Examiner* — Jagadishwar R Samala
(74) *Attorney, Agent, or Firm* — Boyle Fredrickson S.C.

(57) ABSTRACT

It is disclosed herein that that certain alkylphosphocholine analogs are preferentially taken up by multiple myeloma tumor cells. The alkylphophocholine analogs are compounds having the formula:

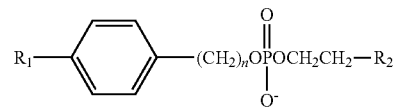

or salts thereof, wherein n is an integer from 12 to 24; and $R_2$ is $-N^+H_3$, $-N^+H_2X$, $-N^+HX_2$, or $-N^+HX_3$, wherein each X is independently $-CH_3$ or $-C_2H_5$. The compounds can be used to treat multiple myeloma or to detect multiple myeloma. In therapeutic treatment, $R_1$ includes a radionuclide that locally delivers therapeutic dosages of radiation to the multiple myeloma tumors cells that preferentially take up the compound. In detection/imaging applications, $R_1$ includes a detection moiety, such as a fluorophore or a radiolabel.

20 Claims, 17 Drawing Sheets
(14 of 17 Drawing Sheet(s) Filed in Color)

CLR1502

ALKYLPHOSPHOCHOLINE ANALOGS FOR MULTIPLE MYELOMA IMAGING AND THERAPY

CROSS-REFERENCE TO RELATED APPLICATIONS

This application claims the benefit of U.S. provisional Application No. 62/145,732, filed on Apr. 10, 2016, which is incorporated by reference herein in its entirety.

STATEMENT REGARDING FEDERALLY SPONSORED RESEARCH OR DEVELOPMENT

This invention was made with government support under CA155192 awarded by the National Institutes of Health. The government has certain rights in the invention.

FIELD OF THE DISCLOSURE

This disclosure relates generally to disease treatment and medical diagnosis/imaging. In particular, the disclosure is directed to the use of alkyphosphocholine analogs to target and treat multiple myeloma, and to related methods of detecting/imaging multiple myeloma tumor cells.

BACKGROUND

It has been shown that alkylphosphocholine analogs are preferentially taken up and retained by solid tumor cancer cells, as compared to normal cells, such as fibroblasts. Accordingly, the use of alkylphoshocholine analogs in methods for imaging and treating cancerous solid tumors has previously been disclosed.

In U.S. Patent Publication No. 2014/0030187, which is incorporated by reference herein in its entirety, Weichert et al. disclose using analogs of the base compound 18-(p-iodophenyl)octadecyl phosphcholine (CLR1404; see FIG. 1) for detecting and locating, as well as for treating, solid tumor cancers. For example, if the iodo moiety is an imaging-optimized radionucleide, such as iodine-124 ($[^{124}I]$-CLR1404), the analog can be used in positron emission tomography-computed tomography (PET/CT) or single-photon emission computed tomography (SPECT) imaging of solid tumors, or in other imaging/detection applications. Alternatively, if the iodo moiety is a radionuclide optimized for delivering therapeutic doses of radiation to the solid tumors cells in which the analog is taken up, such as iodine-125 or iodine-131 ($[^{125}I]$-CLR1404 or $[^{131}I]$-CLR1404), the analog can be used to treat the solid tumors.

In U.S. Patent Publication No. 2010/0284929, which is incorporated by reference herein in its entirety, Pinchuk et al. extend this idea to the visual detection of solid tumors. Specifically, Pinchuk et al. disclose further analogs of CLR1404, wherein the iodo moiety is substituted with a fluorophore. For example, if the iodo moiety is substituted with a boron-dipyrromethene (BODIPY) core (4,4-difluoro-4-bora-3a,4a-diaza-s-indacene), the resulting compound (CLR1501; see FIG. 2) is taken up by solid tumor cells, which can then be visually detected/imaged. CLR1404 analogs having other fluorphores substituted for the iodo moiety, such as IR-775 (CLR1502; see FIG. 3), can similarly be used to visually identify/detect solid tumors or cells from non-solid tumors.

Multiple myeloma (MM) is a type of cancer that occurs in circulating blood cells (i.e., plasma B cells), rather than in solid tissue. Multiple myeloma is a universally fatal disease, comprising 15% of hematological malignancies and 1% of all cancers. It has a median survival of 5-7 years from diagnosis. While newer drugs, such as bortezomib and lenalidomide, have exhibited increased response to therapy, patients inevitably relapse and become resistant to therapy.

Multiple myeloma tumor cells have been shown to be highly radiosensitive; however, there are currently no mechanisms of targeted delivery of radiation to the tumor cells. Therefore, radiotherapy with either radiation or radiolabeled compounds is not currently utilized for the clinical treatment of multiple myeloma.

Accordingly, there is a need for new and effective methods of targeting therapies, particularly radiotherapies, to multiple myeloma tumor cells, and for new methods of detecting/imaging multiple myeloma tumor cells within a patient.

BRIEF SUMMARY

The inventors have discovered that certain alkylphosphocholine analogs are preferentially taken up by multiple myeloma tumor cells, as compared to non-tumor cells. The inventors have further demonstrated that preferential uptake of such compounds can be used in the therapeutic treatment of multiple myeloma, as well as in multiple myeloma detection/imaging applications. In therapeutic treatment, the alkylphosphocholine targeting backbone includes a radionuclide that locally delivers therapeutic dosages of radiation to the multiple myeloma tumors cells that preferentially take up the alkylphosphocholine analog. In detection/imaging applications, the alkylphosphocholine targeting backbone includes a detection moiety, such as a fluorophore or a radiolabel.

Accordingly, in a first aspect, the disclosure encompasses a method of treating multiple myeloma in a subject having multiple myeloma. The method includes the step of administering to a subject having multiple myeloma an effective amount of a compound having the formula:

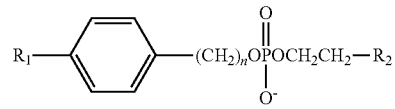

or a salt thereof, wherein $R_1$ comprises a radionuclide; n is an integer from 12 to 24; and $R_2$ is $-N^+H_3$, $-N^+H_2X$, $-N^+HX_2$, or $-N^+HX_3$, wherein each X is independently $-CH_3$ or $-C_2H_5$.

In some embodiments, $R_1$ is a radioactive halogen isotope. In some such embodiments, the halogen is iodine. In some such embodiments, the radioactive iodine isotope is $^{124}I$, $^{125}I$ or $^{131}I$.

In some embodiments, n is 18.
In some embodiments, $R_2$ is $-N^+HX_3$.
In some embodiments, each X is $-CH_3$.
In some embodiments, n is 18, $R_2$ is $-N^+X_3$, and each X is $-CH_3$. In some embodiments, the radioactive iodine isotope is $^{131}I$ (i.e., the compound is $[^{131}I]$-CLR1404).

In some embodiments, $R_1$ comprises an alpha emitter. Exemplary alpha emitters that could be used include, without limitation, Lu-177, Bi-213, Ac-225, Th-227, or As-211. In some such embodiments, the alpha emitter is bound to the compound by chelation. In some such embodiments, $R_1$ further comprises a chelating agent. Exemplary chelating agents that could be used include, without limitation, 1,4,7, 10-tetraazacyclododecane-1,4,7,10-tetraacetic acid (DOTA), diethylene triamine pentaacetic acid (DTPA) variants, such as cDTPA or DTPA-CHX-A, or triethylenetetramine (TETA).

In some embodiments, the compound is administered by oral, parenteral, intranasal, sublingual, rectal, or transdermal delivery.

In some embodiments, the subject is a human.

In a second aspect, the disclosure encompasses a method for inhibiting the proliferation or growth of multiple myeloma tumor cells. The method includes the step of contacting one or more multiple myeloma tumor cells with an effective amount of a compound having the formula:

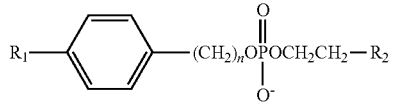

or a salt thereof, wherein $R_1$ comprises a radionuclide; n is an integer from 12 to 24; and $R_2$ is selected from the group consisting of $-N^+H_3$, $-N^+H_2X$, $-N^+HX_2$, and $-N^+HX_3$, wherein each X is independently $-CH_3$ or $-C_2H_5$.

In some embodiments, $R_1$ is a radioactive halogen isotope. In some such embodiments, the halogen is iodine. In some such embodiments, the radioactive iodine isotope is $^{124}I$, $^{125}I$ or $^{131}I$. In some such embodiments, the radioactive iodine isotope is $^{131}I$.

In some embodiments, $R_1$ can be an alpha emitter, such as Lu-177, Bi-213, Ac-225, Th-227, As-211. In some such embodiments, the alpha emitter is bound to the APC analog by means of e.g. a chelating agent (including, but not limited to, DOTA, cDTPA, DTPA-CHX-A or TETA).

In some embodiments, n is 18.

In some embodiments, $R_2$ is $-N^+HX_3$. In some such embodiments, each X is $-CH_3$.

In some embodiments, n is 18, $R_2$ is $-N^+X_3$, and each X is $-CH_3$. In some such embodiments, the radioactive iodine isotope is $^{131}I$ (the compound is $[^{131}I]$-CLR1404).

In some embodiments, the method is performed in vivo, ex vivo, or in vitro.

In a third aspect, the disclosure encompasses a method for detecting or imaging one or more multiple myeloma tumor cells in a biological sample. The method includes the steps of (a) contacting the biological sample with a compound having the formula:

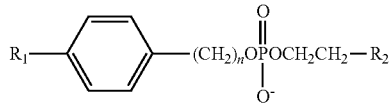

or a salt thereof, wherein $R_1$ comprises a radionuclide or a fluorophore; n is an integer from 12 to 24; and $R_2$ is selected from the group consisting of $-N^+H_3$, $-N^+H_2X$, $-N^+HX_2$, and $-N^+HX_3$, wherein each X is independently $-CH_3$ or $-C_2H_5$, whereby the compound is differentially taken up by multiple myeloma tumor cells within the biological sample; and (b) identifying individual cells or regions within the biological sample that are emitting signals characteristic of the radionuclide or fluorophore, whereby one or more multiple myeloma tumor cells are detected or imaged.

In some embodiments, $R_1$ is a fluorophore, and the signals characteristic of the fluorophore comprise optical signals. In some such embodiments, the fluorophore is BODIPY or IR-775. In some such embodiments, the compound is CLR1501 or CLR1502.

In some embodiments, $R_1$ is a radionuclide capable of emitting electrons, gamma rays, x-rays, positrons, or alpha particles. In some such embodiments, the step of identifying individual cells or regions within the biological sample that are emitting signals characteristic of the radionuclide is performed by positron emission tomography (PET) imaging, single-photon emission computed tomography (SPECT) imaging, or gamma camera planar imaging.

In some embodiments, the radionuclide is a radioactive halogen isotope. In some such embodiments, the halogen is iodine. In some such embodiments, the radioactive iodine isotope is $^{123}I$, $^{124}I$, $^{125}I$ or $^{131}I$. In some such embodiments, the compound is $[^{124}I]$-CLR1404.

In some embodiments, n is 18.

In some embodiments, $R_2$ is $-N^+HX_3$. In some such embodiments, each X is $-CH_3$.

In some embodiments, the biological sample is part or all of a subject. In some embodiments, the biological sample is obtained from a subject. In some such embodiments, the subject is a human.

In a fourth aspect, the disclosure encompasses a method of diagnosing multiple myeloma in a subject. The method includes the steps of performing the detection or imaging as described above, wherein the biological sample is obtained from, part of, or all of a subject. If myeloma tumor cells are detected or imaged by the method, the subject is diagnosed with multiple myeloma.

Other objects, features and advantages of the present invention will become apparent after review of the specification, claims and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

I. In General

Figure 1:
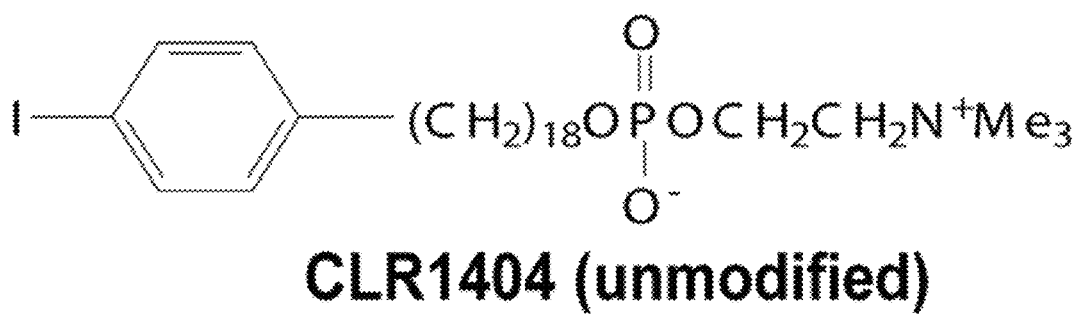
FIG. 1 shows the chemical structure of the base compound 18-(p-iodophenyl)octadecyl phosphcholine (CLR1404).
Figure 2:
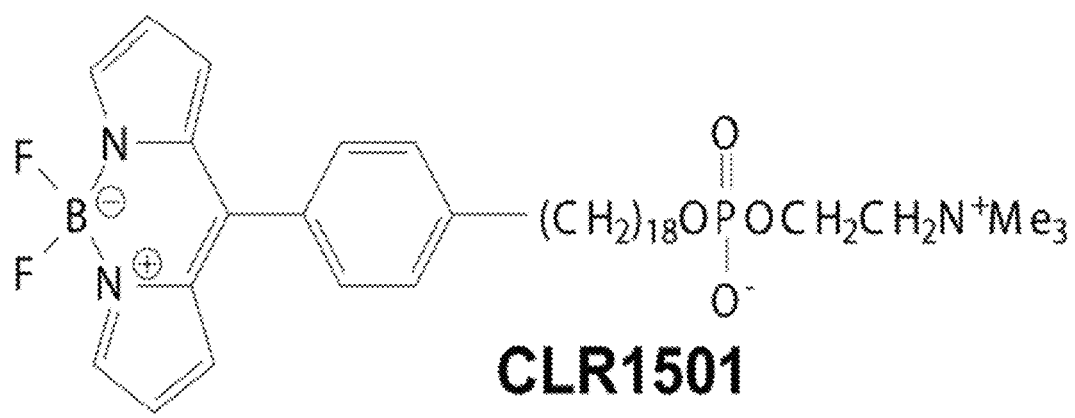
FIG. 2 shows the chemical formula of CLR1501, which is an analog of CLR1404 wherein the iodo moiety is substituted with a fluorescent boron-dipyrromethene (BODIPY) core (4,4-difluoro-4-bora-3a,4a-diaza-s-indacene).
Figure 3:
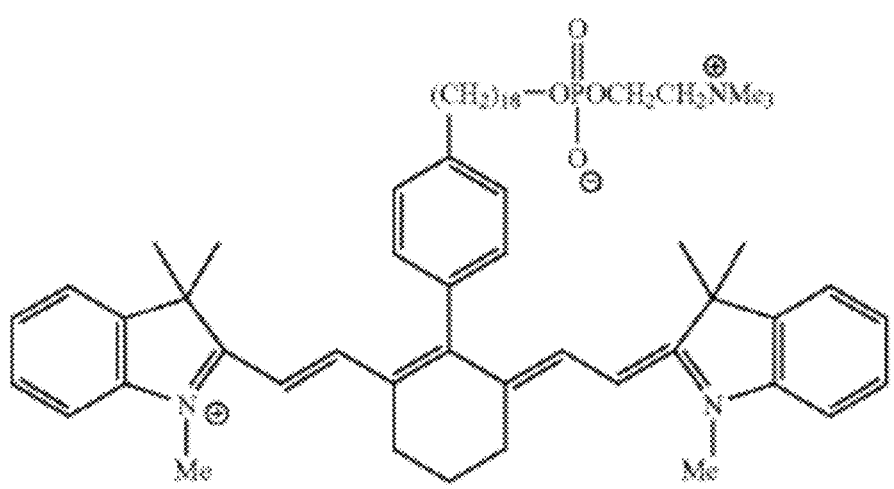
FIG. 3 shows the chemical formula of CLR1502, which is an analog of CLR1404 wherein the iodo moiety is substituted with the fluorophore IR-775.

It is understood that this disclosure is not limited to the particular methodology, protocols, materials, and reagents described, as these may vary. The terminology used herein is for the purpose of describing particular embodiments only, and is not intended to limit the scope of the present invention, which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art.

The terminology as set forth herein is for description of the embodiments only and should not be construed as limiting of the invention as a whole. Unless otherwise specified, "a," "an," "the," and "at least one" are used interchangeably and mean one or more than one.

The disclosure is inclusive of the compounds described herein (including intermediates) in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

"Pharmaceutically acceptable" as used herein means that the compound or composition or carrier is suitable for administration to a subject to achieve the treatments described herein, without unduly deleterious side effects in light of the necessity of the treatment.

The term "therapeutically effective amount" or "pharmaceutically appropriate dosage," as used herein, refers to the amount of the compounds or dosages that will elicit the biological or medical response of a subject, tissue or cell that is being sought by the researcher, veterinarian, medical doctor or other clinician.

As used herein, "pharmaceutically-acceptable carrier" includes any and all dry powder, solvents, dispersion media, coatings, antibacterial and antifungal agents, isotonic agents, absorption delaying agents, and the like. Pharmaceutically-acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include, various lactose, mannitol, oils such as corn oil, buffers such as PBS, saline, polyethylene glycol, glycerin, polypropylene glycol, dimethylsulfoxide, an amide such as dimethylacetamide, a protein such as albumin, and a detergent such as Tween 80, mono- and oligopolysaccharides such as glucose, lactose, cyclodextrins and starch.

The term "administering" or "administration," as used herein, refers to providing the compound or pharmaceutical composition of the invention to a subject suffering from or at risk of the diseases or conditions to be treated or prevented.

A route of administration in pharmacology is the path by which a drug is taken into the body. Routes of administration may be generally classified by the location at which the substance is applied. Common examples may include oral and intravenous administration. Routes can also be classified based on where the target of action is. Action may be topical (local), enteral (system-wide effect, but delivered through the gastrointestinal tract), or parenteral (systemic action, but delivered by routes other than the GI tract), via lung by inhalation.

A topical administration emphasizes local effect, and substance is applied directly where its action is desired. Sometimes, however, the term topical may be defined as applied to a localized area of the body or to the surface of a body part, without necessarily involving target effect of the substance, making the classification rather a variant of the classification based on application location. In an enteral administration, the desired effect is systemic (non-local), substance is given via the digestive tract. In a parenteral administration, the desired effect is systemic, and substance is given by routes other than the digestive tract.

Non-limiting examples for topical administrations may include epicutaneous (application onto the skin), e.g., allergy testing or typical local anesthesia, inhalational, e.g. asthma medications, enema, e.g., contrast media for imaging of the bowel, eye drops (onto the conjunctiva), e.g., antibiotics for conjunctivitis, ear drops, such as antibiotics and corticosteroids for otitis externa, and those through mucous membranes in the body.

Enteral administration may be administration that involves any part of the gastrointestinal tract and has systemic effects. The examples may include those by mouth (orally), many drugs as tablets, capsules, or drops, those by gastric feeding tube, duodenal feeding tube, or gastrostomy, many drugs and enteral nutrition, and those rectally, various drugs in suppository.

Examples of parenteral administrations may include intravenous (into a vein), e.g. many drugs, total parenteral nutrition intra-arterial (into an artery), e.g., vasodilator drugs in the treatment of vasospasm and thrombolytic drugs for treatment of embolism, intraosseous infusion (into the bone marrow), intra-muscular, intracerebral (into the brain parenchyma), intracerebroventricular (into cerebral ventricular system), intrathecal (an injection into the spinal canal), and subcutaneous (under the skin). Among them, intraosseous infusion is, in effect, an indirect intravenous access because the bone marrow drains directly into the venous system. Intraosseous infusion may be occasionally used for drugs and fluids in emergency medicine and pediatrics when intravenous access is difficult.

As used herein, the term "intraperitoneal injection" or "IP injection" refers to the injection of a substance into the peritoneum (body cavity). IP injection is more often applied to animals than to humans. In general, IP injection may be preferred when large amounts of blood replacement fluids are needed, or when low blood pressure or other problems prevent the use of a suitable blood vessel for intravenous injection.

II. The Invention

In certain aspects, the disclosure is directed to the use of fluorescently labeled or radiolabeled alkylphosphocholine analogs for medical detection or detection/imaging of multiple myeloma tumor cells in a subject or in a biological sample. In other aspects, the disclosure is directed to the use of radiolabeled alkylphosphocholine analogs to treat multiple myeloma in a subject.

A. Radionuclides for Multiple Myeloma Treatment

For the disclosed methods of therapeutically treating multiple myeloma, any radionuclide known to emit ionizing radiation in a form that would result in the death of cells that take up the radiolabeled analogs can be incorporated into the alkylphosphocholine targeting backbone. Preferably, the radionuclide emits its ionizing radiation in a form that minimizes damage to tissue outside of the cells that take up the radiolabeled analogs. Such therapeutic treatment encompasses both direct therapy and potential use as myeloablative treatment before bone marrow transplant.

In one non-limiting example, the incorporated radionuclide is iodine-131. Iodine-131, which emits therapeutically effective beta and gamma radiation, has been used with great efficacy in the targeted treatment of thyroid cancer. In another non-limiting example, the radionuclide may be iodine-125, which has the advantage of emitting low-energy gamma/X-ray irradiation Auger electrons, all of which act at a very limited treatment distance, thus sparing surrounding healthy tissue from radiation exposure. In yet another non-limiting example, the radionuclide used is iodine-124.

B. Fluorescent Labels for Multiple Myeloma Detection/Imaging

For the disclosed methods of detecting/imaging multiple myeloma, any fluorophore known to emit optical signals in a form that is readily detectable by conventional optical imaging means may be incorporated into the targeting backbone. Non-limiting examples of "conventional imaging means" include, without limitation, fluorescence microscopy, flow cytometry, endoscopy, and preclinical near infrared fluorescence imaging. Non-limiting examples of fluorophores that could be incorporated include BODIPY and IR-775.

C. Radiolabels for Multiple Myeloma Detection/Imaging

For the disclosed methods of detecting/imaging multiple myeloma, any radionuclide known to emit radiation in a form that is readily detectable by conventional imaging means can be incorporated into the targeting backbone. Non-limiting examples of "conventional imaging means" include gamma ray detection, PET scanning, and SPECT scanning. Non-limiting examples of radionuclides that could be used include iodine-124, iodine-125, and iodine-131.

D. Methods of Synthesizing the Disclosed Analogs

The alkylphosphocholine analogs used in the disclosed methods are known in the art, as are methods of synthesizing such analogs. For details regarding synthetic materials and methods, see, e.g., U.S. Patent Publication Nos. 2010/0284929, 2010/0316567, 2012/0128596, 2014/0030187, and 2014/0023587, each of which is incorporated by reference herein in its entirety.

E. In Vitro Use of Optical Compounds

The disclosed compounds comprising a fluorophore (optical compounds) can be used in a variety of detection methods, including, for example, in endoscopic examination and detection. Such compounds may also be used for in vitro detection of multiple myeloma cells, as illustrated in more detail in the Examples below.

F. Dosage Forms and Administration Methods

Any route of administration may be suitable for administering the disclosed alkylphosphocholine analogs to a subject. In one embodiment, the disclosed alkylphosphocholine analogs may be administered to the subject via intravenous injection. In another embodiment, the disclosed alkylphosphocholine analogs may be administered to the subject via any other suitable systemic deliveries, such as oral, parenteral, intranasal, sublingual, rectal, or transdermal administrations.

In another embodiment, the disclosed alkylphosphocholine analogs may be administered to the subject via nasal systems or mouth through, e.g., inhalation.

In another embodiment, the disclosed alkylphosphocholine analogs may be administered to the subject via intraperitoneal injection or IP injection.

In certain embodiments, the disclosed alkylphosphocholine analogs may be provided as pharmaceutically acceptable salts. Other salts may, however, be useful in the preparation of the alkylphosphocholine analogs or of their pharmaceutically acceptable salts. Suitable pharmaceutically acceptable salts include, without limitation, acid addition salts which may, for example, be formed by mixing a solution of the alkylphosphocholine analog with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

Where the disclosed alkylphosphocholine analogs have at least one asymmetric center, they may accordingly exist as enantiomers. Where the disclosed alkylphosphocholine analogs possess two or more asymmetric centers, they may additionally exist as diastereoisomers. It is to be understood that all such isomers and mixtures thereof in any proportion are encompassed within the scope of the present disclosure.

The disclosure also includes methods of using pharmaceutical compositions comprising one or more of the disclosed alkylphosphocholine analogs in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid pre-formulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the alkylphosphocholine analogs may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The disclosed alkylphosphocholine analogs are particularly useful when formulated in the form of a pharmaceutical injectable dosage, including in combination with an injectable carrier system. As used herein, injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection.

Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1

Differential Uptake of Alkylphosphocholine Analogs in Multiple Myeloma Cell Lines In this Example, we demonstrate that two analogs of the base compound CLR1404 having a fluorophore substituted for the iodo moiety (CLR1501 and CLR 1502) exhibit high uptake in five different multiple myeloma cell lines: MM.1S, MM.1R, RPM18226, U266, and NCIH929. In contrast, we show that these analogs exhibit minimal to no uptake in human peripheral blood mononuclear cells isolated from normal human blood. Accordingly, this Example demonstrates the potential of using analogs of CLR1404 incorporating a radionuclide moiety to specifically target localized radiation therapy to multiple myeloma tumor cells in a subject, or of using analogs of CLR1404 incorporating a detection moiety, such as a fluorophore or radiolabel, to identify, detect, and/or image multiple myeloma cells.

Figure 4:
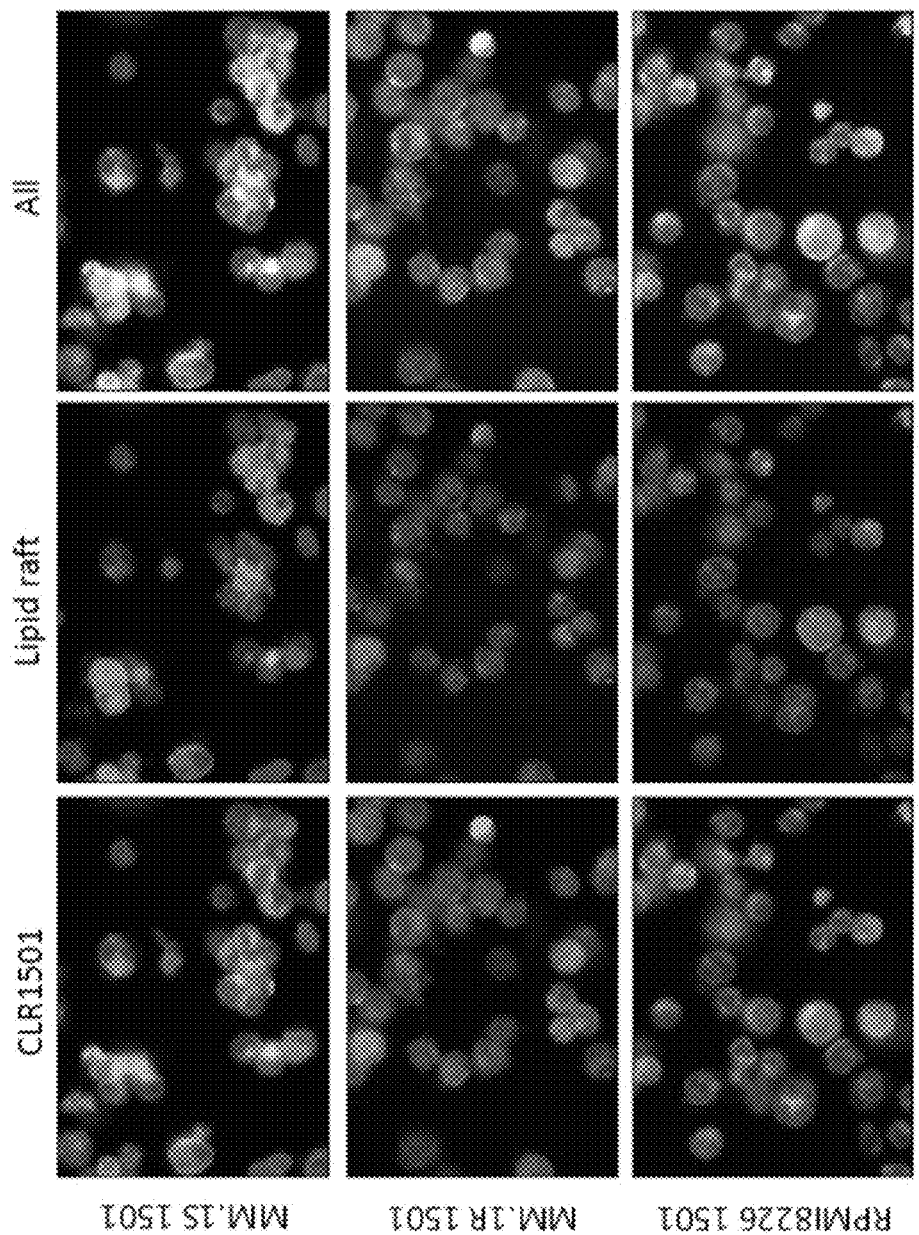
FIG. 4 includes optical images showing uptake of CLR1501 in three different multiple myeloma cell lines (top row, MM.1S; middle row, MM.1R; bottom row, RPM18226). Leftmost column shows uptake in each cell line for cells incubated with CLR1501 (green stain). Center column shows cells incubated with lipid raft stain (red stain—Alexa Fluor-555-labeled cholera toxin subunit B). Rightmost column shows co-uptake in cells incubated with both stains. 20× magnification.
Figure 5:
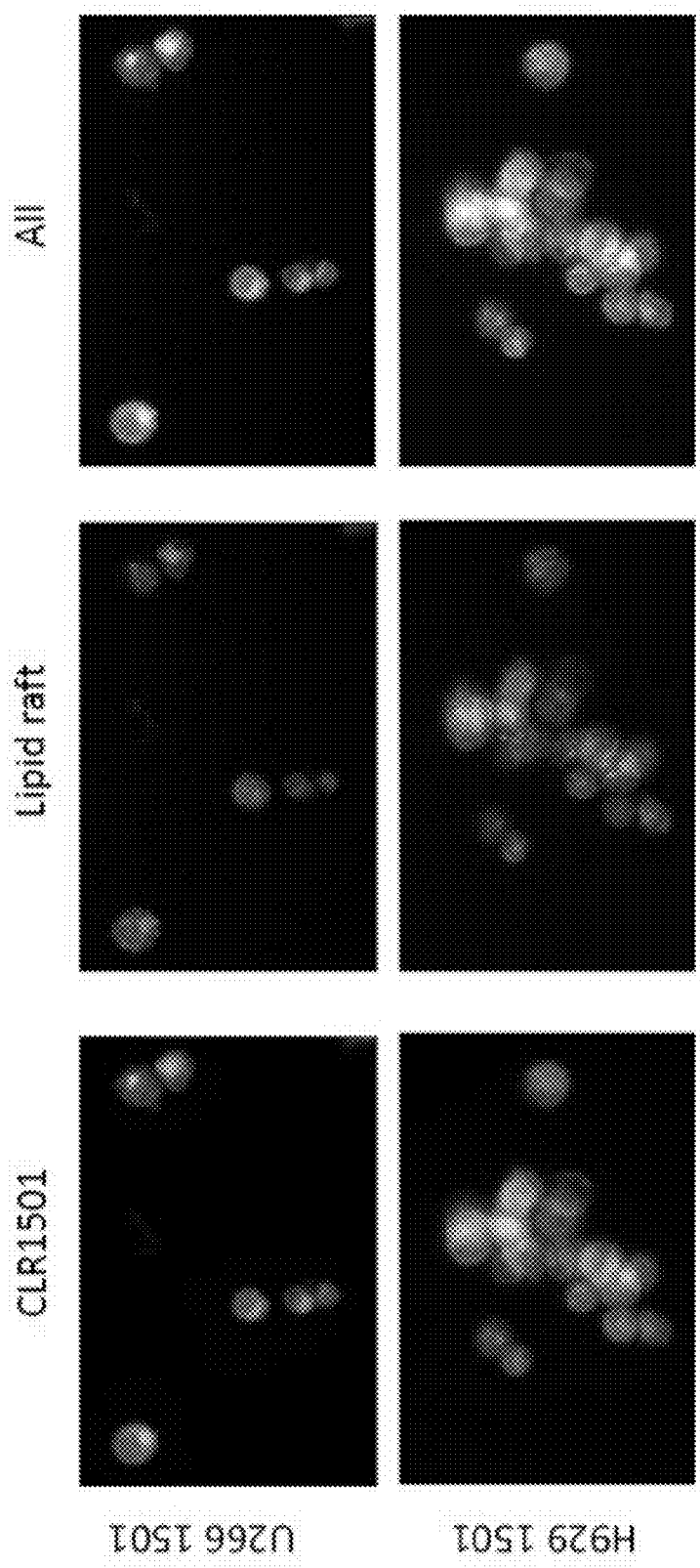
FIG. 5 includes optical images showing uptake of CLR1501 in two additional multiple myeloma cell lines (top row, U266; bottom row, H929). Leftmost column shows uptake in each cell line for cells incubated with CLR1501 (green stain). Center column shows cells incubated with lipid raft stain (red stain—Alexa Fluor-555-labeled cholera toxin subunit B). Rightmost column shows co-uptake in cells incubated with both stains. 20× magnification.
Figure 6:
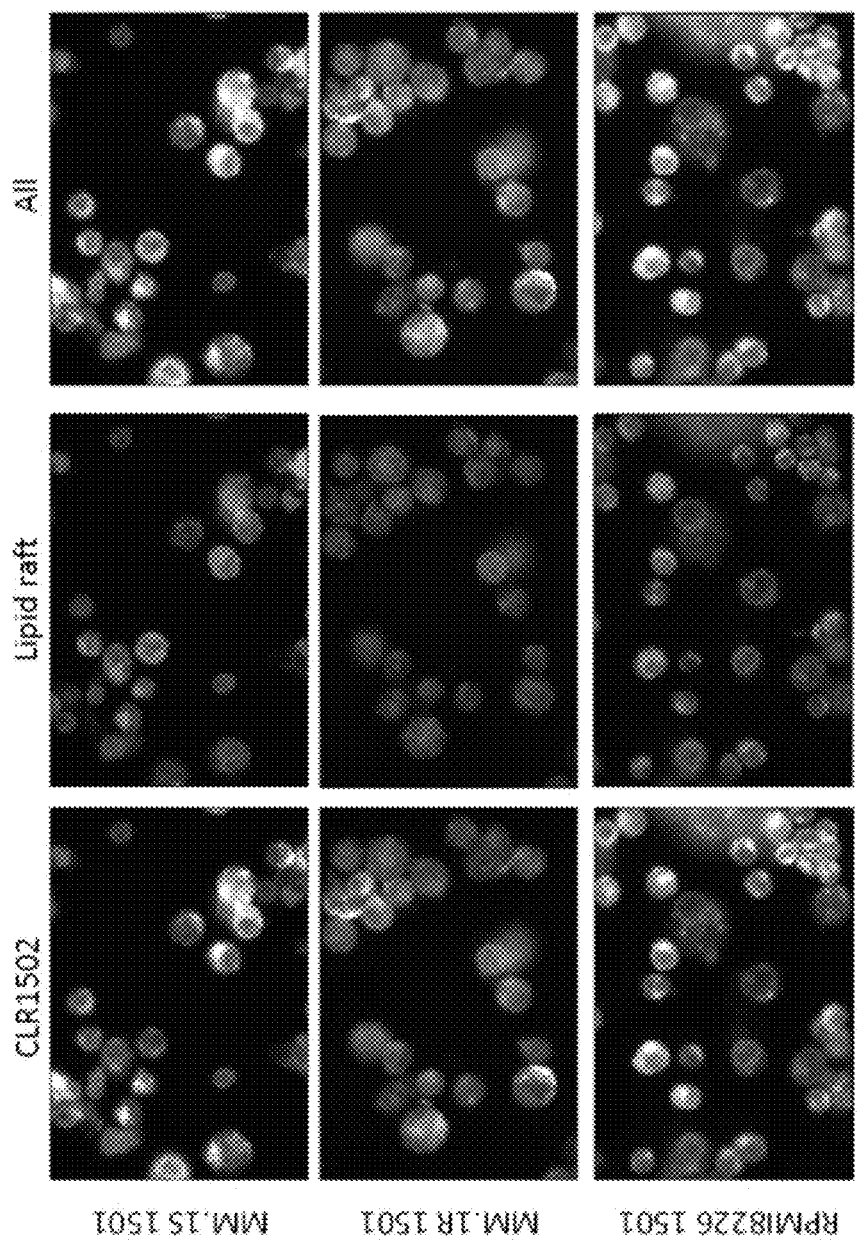
FIG. 6 includes optical images showing uptake of CLR1502 in three different multiple myeloma cell lines (top row, MM1S; middle row, MM.1R; bottom row, RPM18226). Leftmost column shows uptake in each cell line for cells incubated with CLR1502. Center column shows cells incubated with lipid raft stain (red stain—Alexa Fluor-555-labeled cholera toxin subunit B). Rightmost column shows co-uptake in cells incubated with both stains. 20× magnification.
Figure 7:
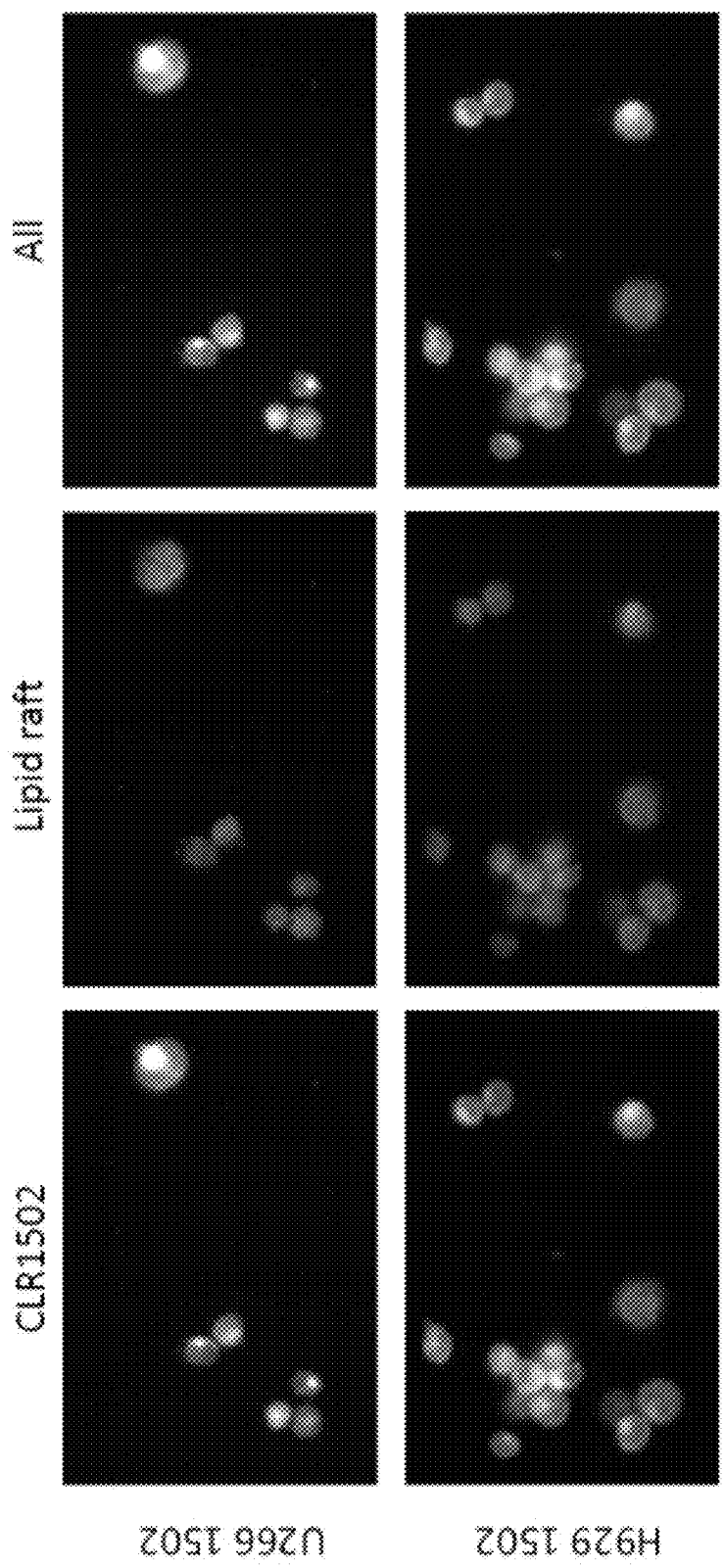
FIG. 7 includes optical images showing uptake of CLR1502 in two additional multiple myeloma cell lines (top row, U266; bottom row, H929). Leftmost column shows uptake in each cell line for cells incubated with CLR1502. Center column shows cells incubated with lipid raft stain (red stain—Alexa Fluor-555-labeled cholera toxin subunit B). Rightmost column shows co-uptake in cells incubated with both stains. 20× magnification.

As shown in FIG. 4, the multiple myeloma cells lines MM.1S, MM.1R, and RPM18226 all exhibit strong uptake of CLR1501 when incubated with CLR1501 or when co-incubated with both CLR1501 and lipid raft stain. Results with lipid raft stain demonstrate that uptake of CLR1501 is localized to the lipid rafts within the multiple myeloma cells. FIG. 5 shows similar results obtained with two other multiple myeloma cell lines: U266, and NCIH929. FIG. 6 shows similar results for the uptake of CLR1502 in the MM1.S, MM.1R; and RPM18226 multiple myeloma cell lines. FIG. 7 shows similar results for the uptake of CLR1502 in the U266, and NCIH929 multiple myeloma cell lines.

Figure 8:
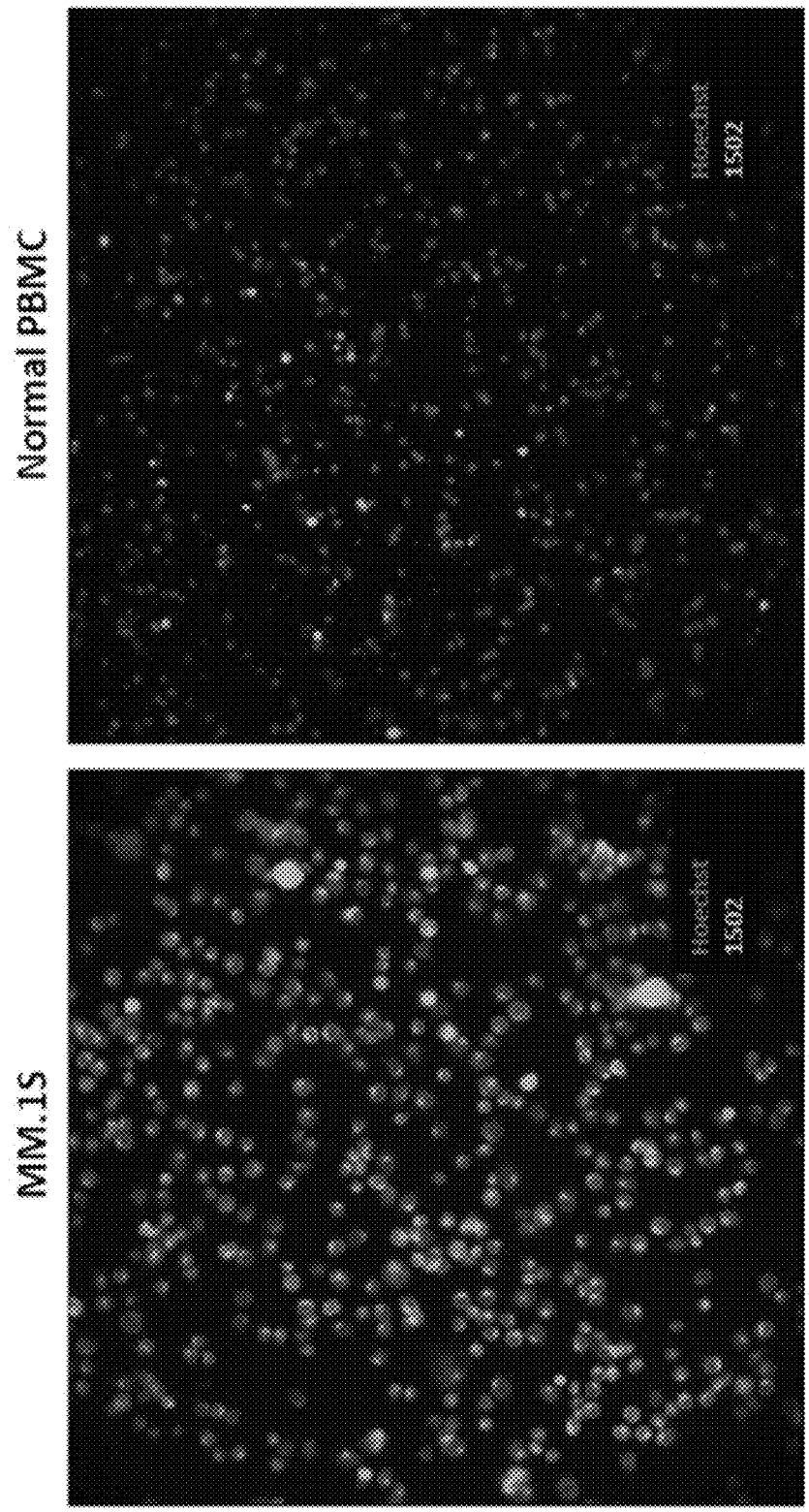
FIG. 8 includes optical images showing uptake of CLR1502 in cells co-incubated with Hoechst 33452 (blue nuclear) stain. The left panel shows uptake in an MM1.S multiple myeloma cell line. The right panel shows uptake in a cell line of normal human mononuclear cells (PBMCs). The PBMCs exhibited minimal uptake of CLR1502, as compared to the multiple myeloma cell line. 20× magnification.

Uptake of CLR1501 and 1502 was assessed using peripheral blood mononuclear cells (PBMCs) isolated from normal human blood. An uptake comparison with cells from the MM1.S multiple myeloma cell line is shown in FIG. 8. As seen in FIG. 8, minimal to no uptake was exhibited by the normal PBMCs (with the exception of $CD14^+$ monocyte/macrophage cells, which did exhibit uptake), as compared to the multiple myeloma cells.

Taken together, these results show that alylphosphocholine analogs can be used to differentially target multiple myeloma cells. The analogs can be designed as targeted agents for local delivery of radiation therapy, or for targeted delivery of detection/imaging moieties, such as fluorophores or radiolabels.

Example 2

Differential Uptake of Alkylphosphocholine Analogs in $CD138^+$ Multiple Myeloma Tumor Cells and $CD14^+$ Monocytes/Macrophages from Multiple Myeloma Patients In this Example, we further demonstrate the differential uptake of CLR1501 and CLR1502 in multiple myeloma tumor cells obtained from five different multiple myeloma patients. The results confirm that the uptake data obtained from cell lines also applies to cells obtained from multiple myeloma patients.

Bone marrow aspirate samples were taken from fifteen different patients diagnosed with multiple myeloma. Consistent the results of Example 1, high uptake of CLR1501 and CLR1502 was exhibited by $CD138^+$ multiple myeloma tumor cells isolated from the aspirate samples, while very minimal to no uptake was seen in CD138-cells isolated from the same patient sample (again, with the exception of $CD14^+$ cells, which did take up the analogs).

Figure 9:
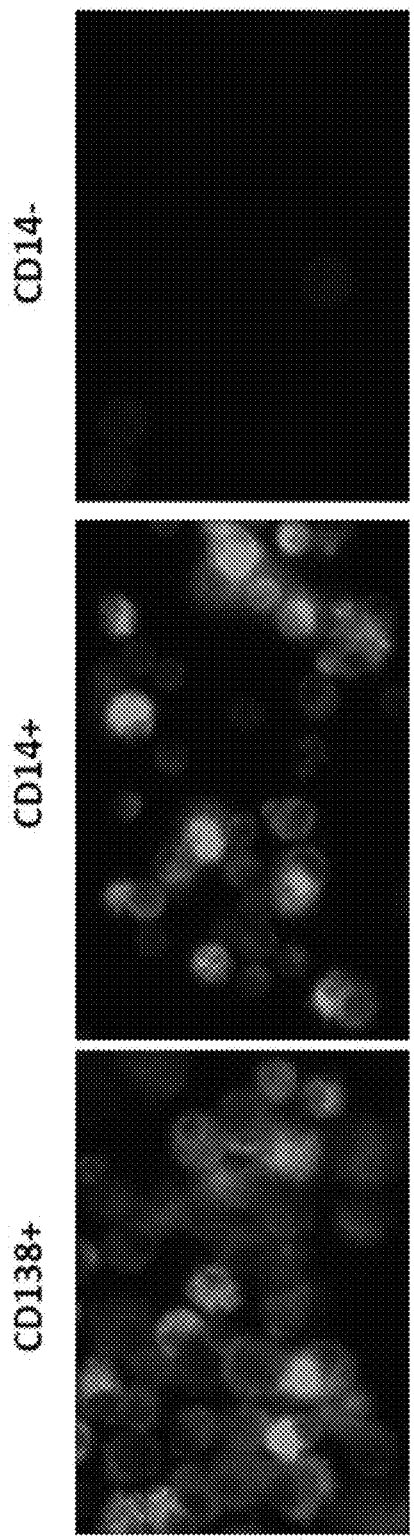
FIG. 9 includes optical images of bone marrow aspirate cells taken from multiple myeloma patient A, showing uptake of CLR1501. The left panel shows uptake in $CD138^+$ multiple myeloma tumor cells isolated from the bone marrow aspirate. The center panel shows uptake in $CD14^+$ monocyte/macrophage cells isolated from the bone marrow aspirate. The right panel shows that no detectable uptake occurred in $CD138^-/CD14^-$ cells (other mononuclear cells) isolated from the bone marrow aspirate. 20× magnification.
Figure 10:
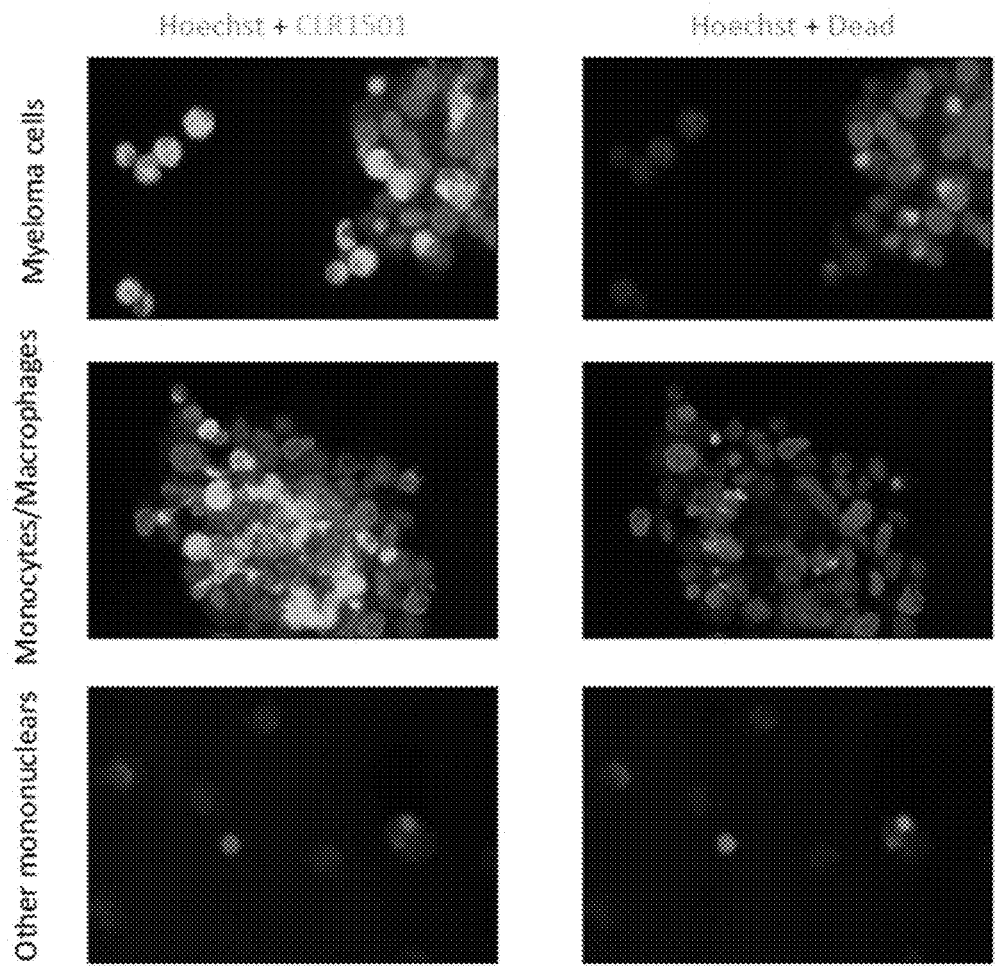
FIG. 10 includes optical images of bone marrow aspirate cells taken from multiple myeloma patient B, showing uptake of CLR1501. The top left panel shows CLR 1501 uptake in $CD138^+$ multiple myeloma tumor cells isolated from the bone marrow aspirate that were co-incubated with Hoechst 33452. The top right panel shows $CD138^+$ multiple myeloma tumor cells isolated from the bone marrow aspirate that were co-incubated with Hoechst 33452 and ethidium homodimer dead cell stain. The center left panel shows CLR1501 uptake in $CD14^-$ monocyte/macrophages isolated from the bone marrow aspirate that were co-incubated with Hoechst 33452. The center right panel shows $CD14^+$ monocyte/macrophages isolated from the bone marrow aspirate that were co-incubated with Hoechst 33452 and ethidium homodimer dead cell stain. The bottom left panel shows minimal CLR1501 uptake in $CD138^-/CD14^-$ cells (other mononuclear cells) isolated from the bone marrow aspirate that were co-incubated with Hoechst 33452. The bottom right panel shows $CD138^-/CD14^-$ cells (other mononuclear cells) isolated from the bone marrow aspirate that were co-incubated with Hoechst 33452 and ethidium homodimer dead cell stain. 20× magnification.

FIG. 9 shows CLR1501 uptake in cells isolated from a bone marrow aspirate from the multiple myeloma patient designated as "patient A." CLR1501 was taken up by $CD138^+$ multiple myeloma tumor cells and $CD14^+$ monocyte/macrophage cells, whereas no detectable uptake occurred in $CD138^-/CD14^-$ cells. FIG. 10 shows similar results obtained using bone marrow aspirate cells taken from multiple myeloma patient designated as "patient B."

Figure 11:
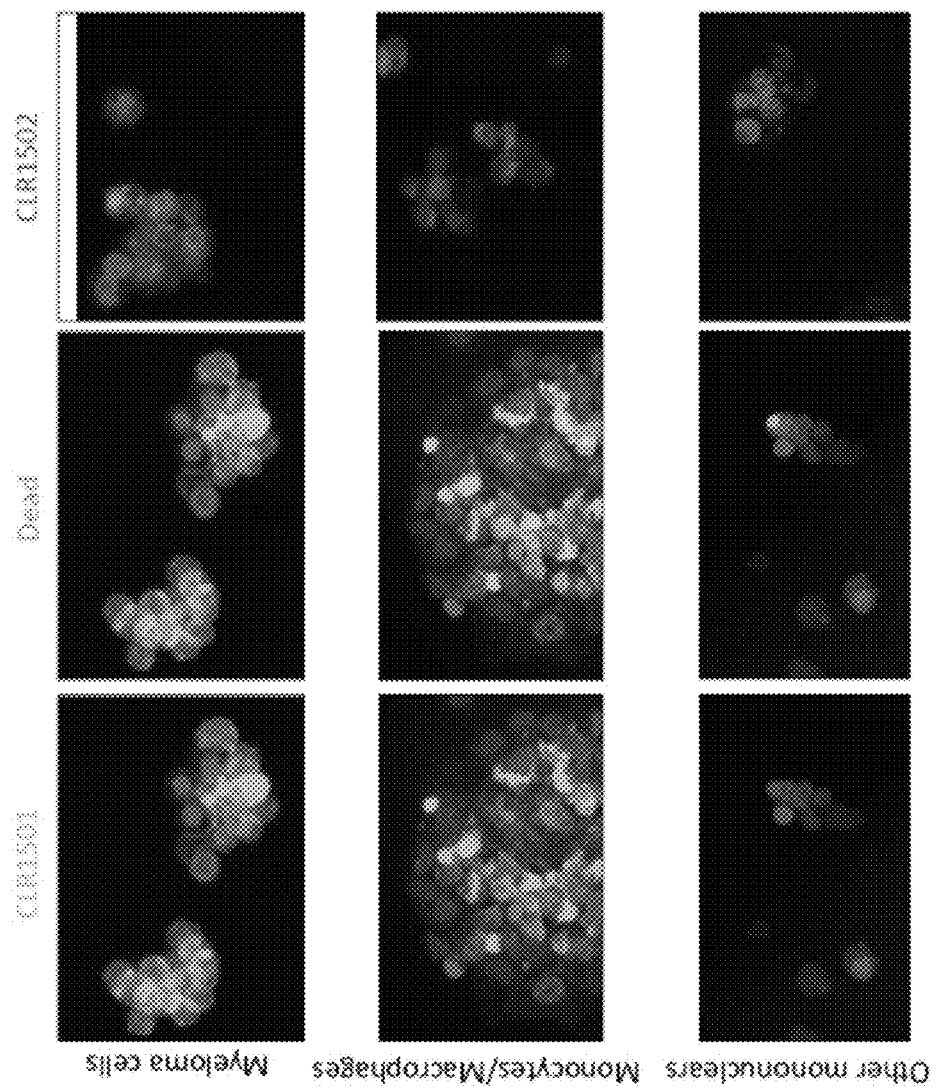
FIG. 11 includes optical images of bone marrow aspirate cells taken from multiple myeloma patient C, showing uptake of both CLR1501 and CLR1502. The top row shows uptake in $CD138^+$ multiple myeloma tumor cells isolated from the bone marrow aspirate of CLR1501 (left panel), CLR1501 and ethidium homodimer dead cell stain (center panel), and CLR1502 (right panel). The center row shows uptake in $CD14^+$ monocytes/macrophages isolated from the bone marrow aspirate of CLR1501 (left panel), CLR1501 and ethidium homodimer cell stain (center panel), and CLR1502 (right panel). The bottom row shows uptake in $CD138^-/CD14^-$ cells (other mononuclear cells) isolated from the bone marrow aspirate of CLR1501 (left panel), CLR1501 and ethidium homodimer dead cell stain (center panel), and CLR1502 (right panel). 20× magnification.

FIG. 11 shows similar results for the uptake of both CLR1501 and CLR1502 obtained using bone marrow aspirate cells taken from multiple myeloma patient designated as "patient C."

Figure 12:
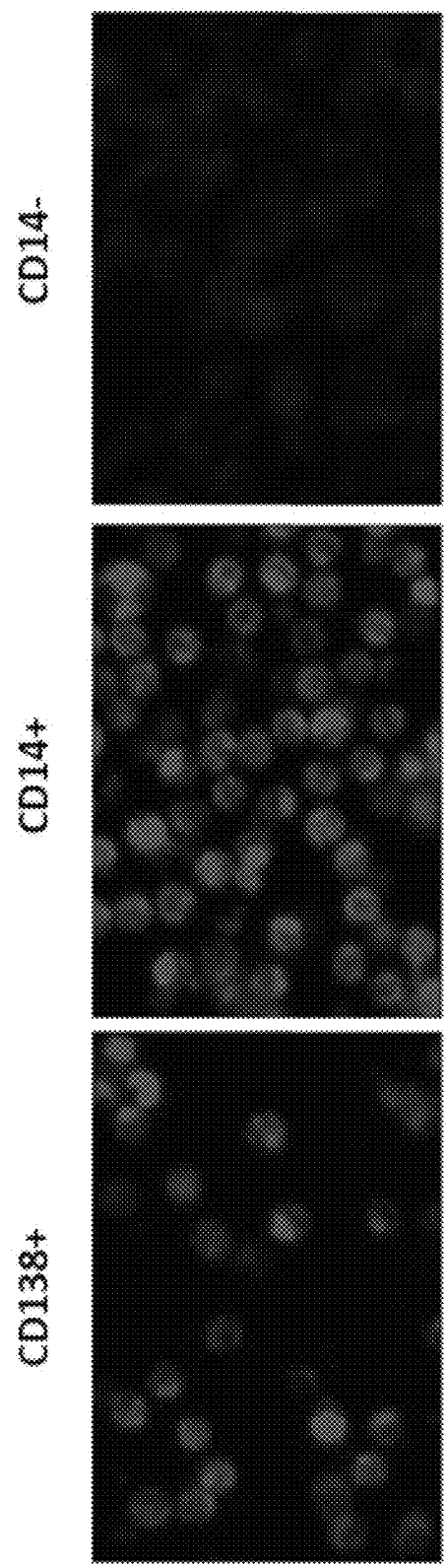
FIG. 12 includes optical images of bone marrow aspirate cells taken from multiple myeloma patient D, showing uptake of CLR1502. The left panel shows uptake in $CD138^+$ multiple myeloma tumor cells isolated from the bone marrow aspirate. The center panel shows uptake in $CD14^+$ monocyte/macrophage cells isolated from the bone marrow aspirate. The right panel shows that minimal uptake occurred in $CD138^-/CD14^-$ cells (other mononuclear cells) isolated from the bone marrow aspirate. 20× magnification.
Figure 13:
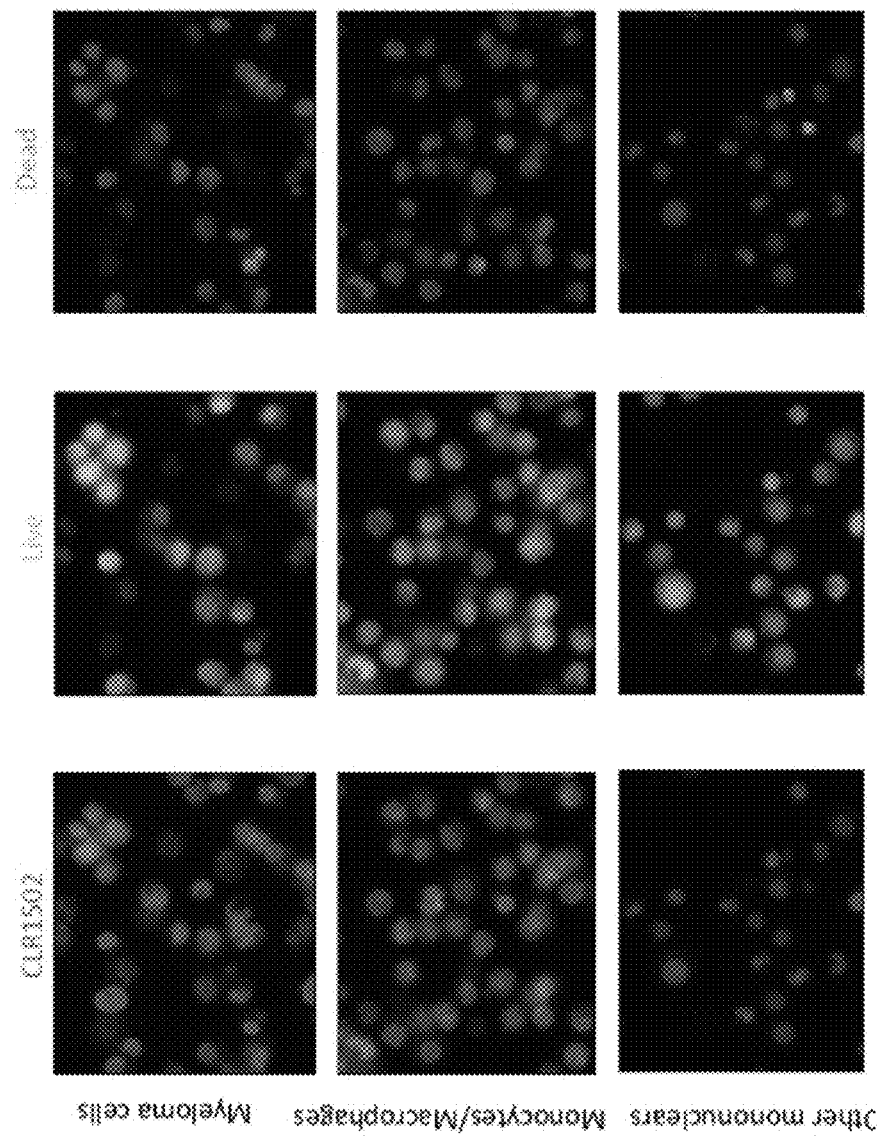
FIG. 13 includes optical images of bone marrow aspirate cells taken from multiple myeloma patient E, showing uptake of CLR1502. The top row shows uptake in $CD138^+$ multiple myeloma tumor cells isolated from the bone marrow aspirate of CLR1502 (left panel), calcein AM live cell stain (center panel), and ethidium homodimer dead cell stain (right panel). The center row shows uptake in $CD14^+$ monocytes/macrophages isolated from the bone marrow aspirate of CLR1502 (left panel), calcein AM live cell stain (center panel), and ethidium homodimer dead cell stain (right panel). The bottom row shows uptake in $CD138^-/CD14^-$ cells (other mononuclear cells) isolated from the bone marrow aspirate of CLR1502 (left panel), calcein AM live cell stain (center panel), ethidium homodimer dead cell stain (right panel). 20× magnification.
Figure 14:
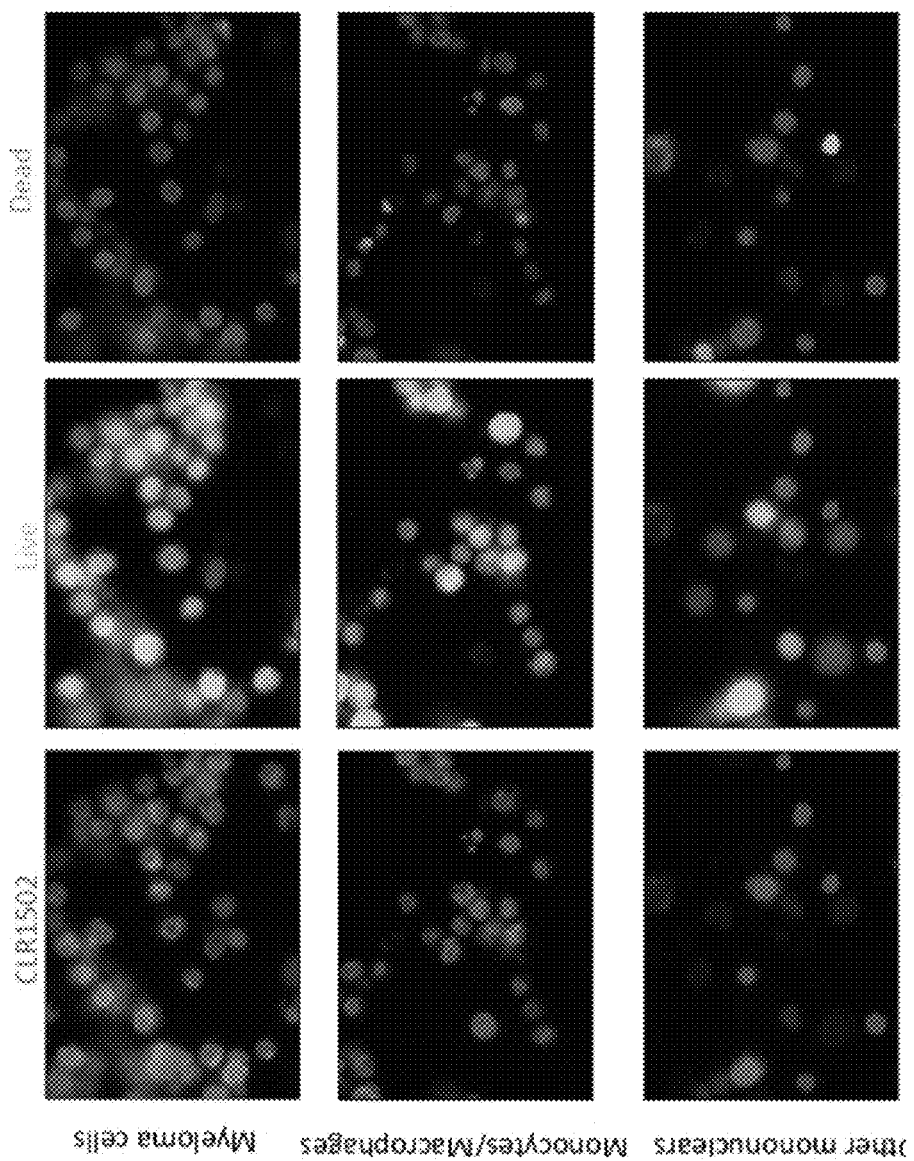
FIG. 14 includes optical images of bone marrow aspirate cells taken from multiple myeloma patient F, showing uptake of CLR1502. The top row shows uptake in $CD138^+$ multiple myeloma tumor cells isolated from the bone marrow aspirate of CLR1502 (left panel), calcein AM live cell stain (center panel), and ethidium homodimerdead cell stain (right panel). The center row shows uptake in $CD14^+$ monocytes/macrophages isolated from the bone marrow aspirate of CLR1502 (left panel), calcein AM live cell stain (center panel), and ethidium homodimer dead cell stain (right panel). The bottom row shows uptake in $CD138^-/CD14^-$ cells (other mononuclear cells) isolated from the bone marrow aspirate of CLR1502 (left panel), calcein AM live cell stain (center panel), ethidium homodimer dead cell stain (right panel). 20× magnification.
Figure 15:
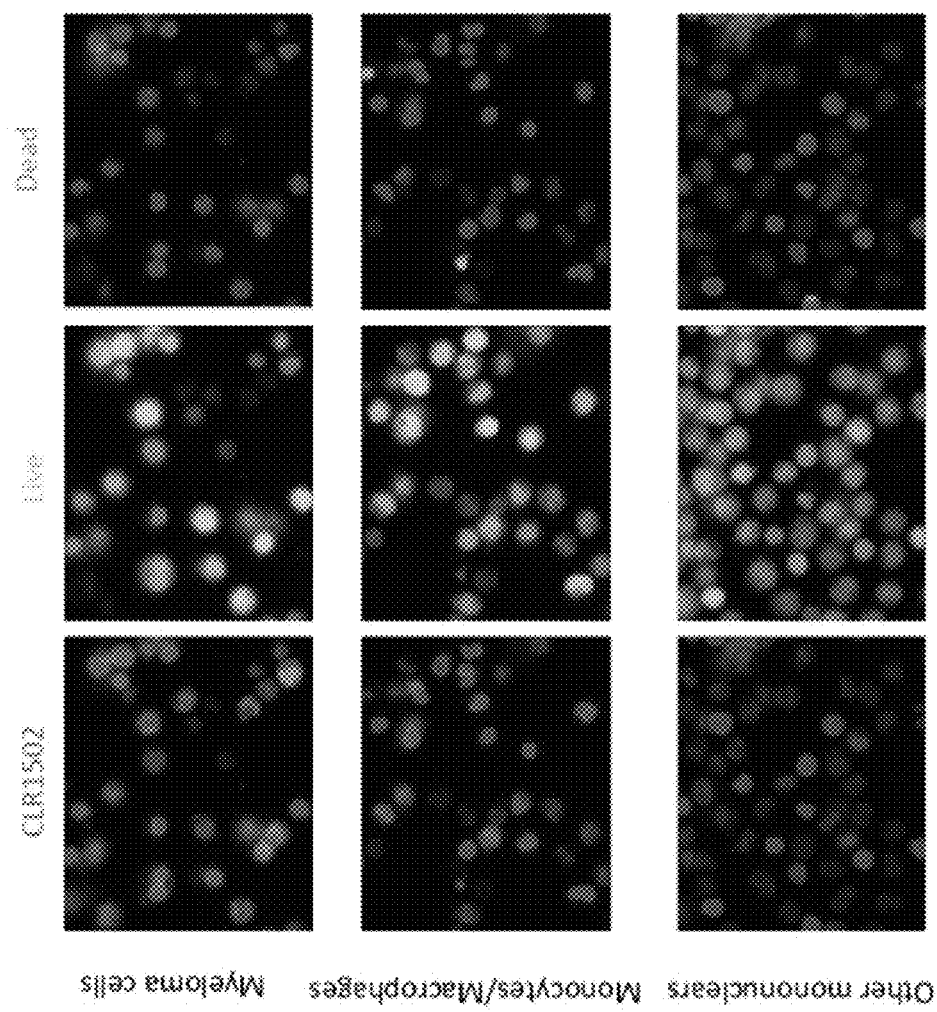
FIG. 15 includes optical images of bone marrow aspirate cells taken from multiple myeloma patient G, showing uptake of CLR1502. The top row shows uptake in $CD138^+$ multiple myeloma tumor cells isolated from the bone marrow aspirate of CLR1502 (left panel), calcein AM live cell stain (center panel), and ethidium homodimer dead cell stain (right panel). The center row shows uptake in $CD14^+$ monocytes/macrophages isolated from the bone marrow aspirate of CLR1502 (left panel), calcein AM live cell stain (center panel), and ethidium homodimer dead cell stain (right panel). The bottom row shows uptake in $CD138^-/CD14^-$ cells (other mononuclear cells) isolated from the bone marrow aspirate of CLR1502 (left panel), calcein AM live cell stain (center panel), ethidium homodimer dead cell stain (right panel). 20× magnification.

FIG. 12 shows similar results for the uptake of CLR 1502 obtained using bone marrow aspirate cells taken from multiple myeloma patient designated as "patient D." FIG. 13 shows similar results for the uptake of CLR 1502 obtained using bone marrow aspirate cells taken from multiple myeloma patient designated as "patient E." FIG. 14 shows similar results for the uptake of CLR1502 obtained using bone marrow aspirate cells taken from multiple myeloma patient designated as "patient F." FIG. 15 shows similar results for the uptake of CLR1502 obtained using bone marrow aspirate cells taken from multiple myeloma patient designated as "patient G."

Figure 16:
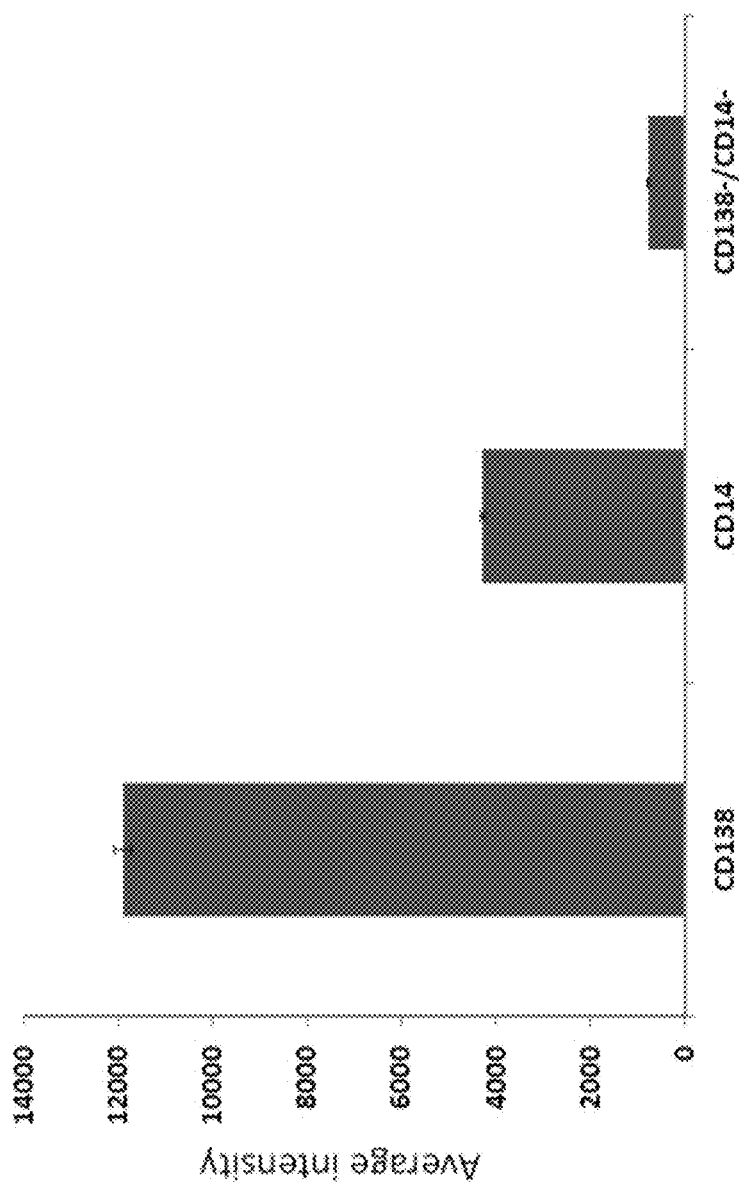
FIG. 16 is a bar graph showing data from the quantification of CLR1502 uptake in bone marrow aspirate cells taken from multiple myeloma patient G. Quantification of uptake was determined by measured fluorescence intensity. Quantification of uptake is shown for isolated $CD138^+$ multiple myeloma tumor cells (leftmost bar), isolated $CD14^+$ monocyte/macrophages (center bar), and isolated $CD138^-/CD14^-$ cells (other mononuclear cells) (rightmost bar).

Uptake of both CLR1501 and CLR1502 was quantified by measuring fluorescence intensity for $CD138^+$ multiple myeloma tumor cells, $CD14^+$ monocyte/macrophage cells, and $CD138^-/CD14^-$ cells isolated from bone marrow aspitrates from multiple myeloma patients. Characteristic results (CR1502 uptake in cells from patient G) are shown in FIG. 16. Uptake of CLR1502 was threefold greater in $CD138^+$ multiple myeloma tumor cells than in $CD14^-$ monocyte/macrophage cells obtained from the same patient, and about fifteen fold greater in $CD138^+$ multiple myeloma tumor cells than in $CD138^-/CD14^-$ cells obtained from the same patient. Overall, fluorescence intensity of CLR1501 and CLR1502 showed a 6-15 fold higher uptake in $CD138^+$ multiple myeloma tumor cells than in $CD138^-/CD14^-$ cells obtained from the same patient.

Together, these results demonstrate that the differential uptake and retention of alkylphosphocholine analogs demonstrated in multiple myeloma cell lines is also exhibited by multiple myeloma cells in clinical patients. Thus, the disclosed methods can readily be applied to clinical therapeutic and imaging applications.

Example 3

Demonstrating the Bioactivity of $[^{131}I]$-CLR1404 Against a Multiple Myeloma Tumor Cell Line In this Example, we demonstrate the efficacy of the disclosed therapeutic strategy in a multiple myeloma cell line. Specifically, the analog $[^{131}I]$-CLR1404, which is differentially taken up and maintained with multiple myeloma cells, contains the radionuclide iodine-131, a radioactive isotope of iodine that locally emits potentially therapeutic doses of beta and gamma radiation. After uptake into the targeted multiple myeloma tumor cells, the locally emitted radiation will differentially kill any multiple myeloma tumor cells that take up the analog. Such bioactivity against multiple myeloma tumor cells is demonstrated in this Example.

Figure 17:
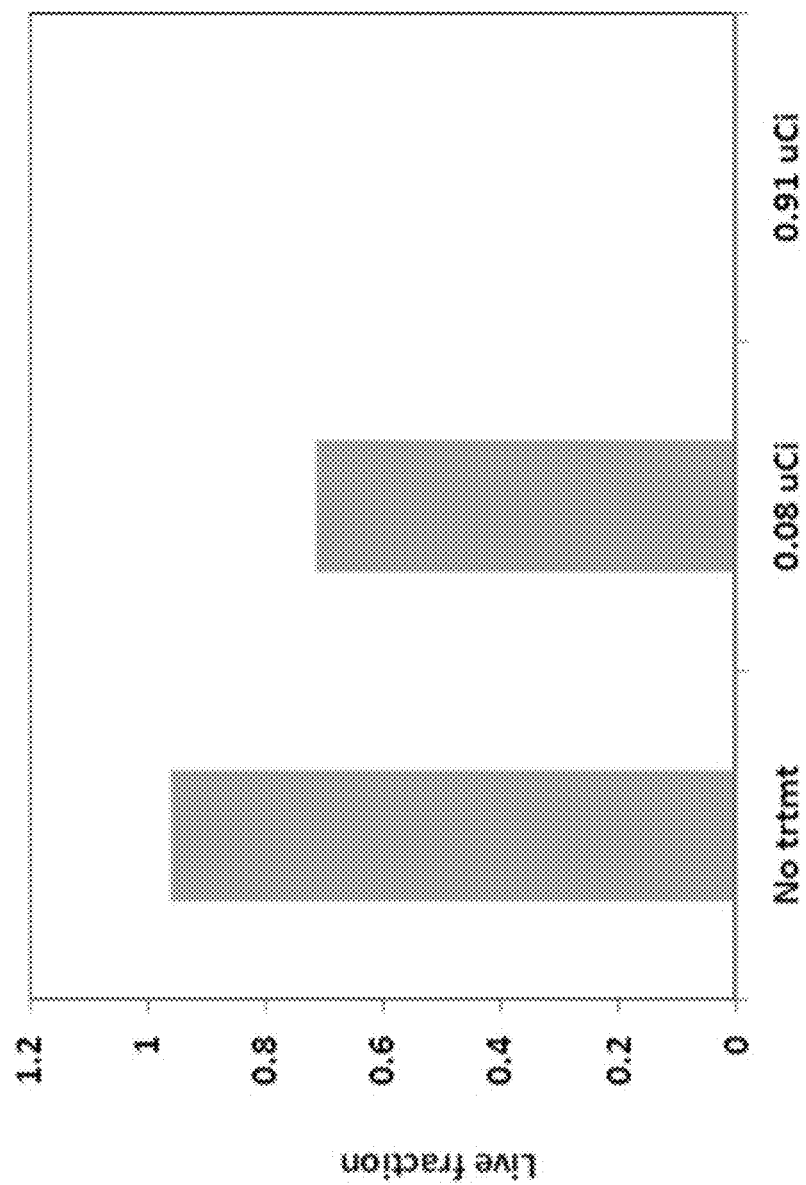
FIG. 17 is a bar graph showing the results of incubating MM.Is multiple myeloma cells with [$^{131}$I]-CLR1404 for a 48 hour period, as compared to a control. The control (no treatment, leftmost bar) maintained 96% live fraction of the multiple myeloma cells, while treatment with 0.082 µCi [$^{131}$I]-CLR1404 reduced live fraction of multiple myeloma cells to 71% (center bar), and treatment with 0.91 µCi [$^{131}$I]-CLR1404 reduced live fraction of multiple myeloma cells to 0% (rightmost bar).

MM.1s multiple myeloma cells were exposed to two different concentrations of $[^{131}I]$-CLR1404 (0.082 μCi and 0.91 μCi) for a 48 hour period, as well as to a control containing no $[^{131}I]$-CLR1404. Bioactivity for each group was determined by determining the percentage of cells that remained alive after the exposure period (live fraction). As shown in FIG. 17, the control group maintained 96% live fraction of the multiple myeloma cells, while treatment with 0.082 μCi $[^{131}I]$-CLR1404 reduced live fraction of multiple myeloma cells to 71%, and treatment with 0.91 μCi $[^{131}I]$-CLR1404 reduced live fraction of multiple myeloma cells to 0%. These results demonstrate the efficacy of using alkylphosocholine analogs to deliver targeted radiotherapy of multiple myeloma cells.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

The invention claimed is:

1. A method for treating multiple myeloma in a subject, comprising administering to a subject having multiple myeloma an effective amount of a compound having the formula:

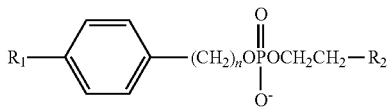

or a salt thereof, wherein:
$R_1$ is a radioactive iodine isotope;
n is an integer from 12 to 24; and
$R_2$ is —$N^+(CH_3)_3$;
whereby multiple myeloma is treated in the subject.

2. The method of claim 1, wherein the radioactive iodine isotope is-selected from the group consisting of $^{124}I$, $^{125}I$ and $^{131}I$.

3. The method of claim 2, wherein the radioactive iodine isotope is $^{125}I$ or $^{131}I$.

4. The method of claim 3, wherein the radioactive iodine isotope is $^{131}I$.

5. The method of claim 1, wherein n is 18.

6. The method of claim 5, wherein the compound is

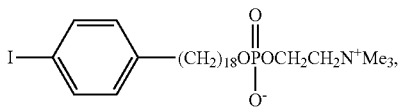

wherein the I is the radioactive iodine isotope $^{131}I$ (the compound is [$^{131}I$]-CLR1404).

7. The method of claim 1, wherein the compound is administered by parentaeral, intranasal, sublingual, rectal, or transdermal delivery.

8. A method for inhibiting the proliferation or growth of multiple myeloma tumor cells, comprising contacting one or more multiple myeloma tumor cells with an effective amount of a compound having the formula:

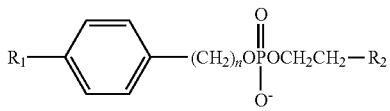

or a salt thereof, wherein:
$R_1$ is a radioactive iodine isotope;
n is an integer from 12 to 24; and
$R_2$ is —$N^+(CH_3)_3$;
whereby growth or proliferation the multiple myeloma tumor cells is inhibited.

9. The method of claim 8, wherein the radioactive iodine isotope is selected from the group consisting of $^{124}I$, $^{125}I$ and $^{131}I$.

10. The method of claim 9, wherein the radioactive iodine isotope is $^{125}I$ or $^{131}I$.

11. The method of claim 10, wherein the radioactive iodine isotope is $^{131}I$.

12. The method of claim 8, wherein n is 18.

13. The method of claim 12, wherein the radioactive iodine isotope is $^{131}I$ (the compound is [$^{131}I$]-CLR1404).

14. The method of claim 8, wherein the method is performed in vivo, ex vivo, or in vitro.

15. A method for detecting or imaging one or more multiple myeloma tumor cells in a biological sample, comprising:
(a) contacting the biological sample with a compound having the formula:

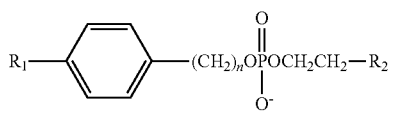

or a salt thereof, wherein:
$R_1$ comprises a radioactive iodine isotope or a fluorophore;
n is an integer from 12 to 24; and
$R_2$ is —$N^+(CH_3)_3$, whereby the compound is differentially taken up by multiple myeloma tumor cells within the biological sample; and
(b) identifying individual cells or regions within the biological sample that are emitting signals characteristic of the radioactive iodine isotope or fluorophore, whereby one or more multiple myeloma tumor cells are detected or imaged.

16. The method of claim 15, wherein $R_1$ is a fluorophore, and wherein the signals characteristic of the fluorophore comprise optical signals.

17. The method of claim 16, wherein the compound is

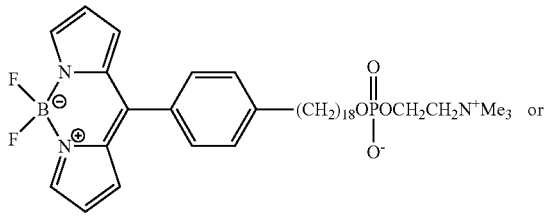

CLR1501

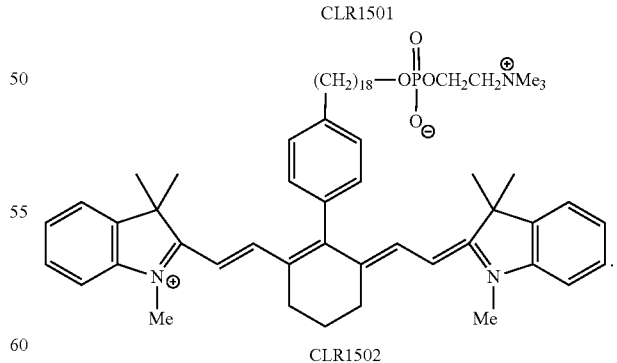

CLR1502

18. The method of claim 15, wherein the radioactive iodine isotope is selected from the group consisting of $^{123}I$, $^{124}I$, $^{125}I$, and $^{131}I$.

19. The method of claim 18, wherein the compound is [$^{124}I$]-CLR1404.

20. A method of diagnosing multiple myeloma in a subject, comprising performing the method of claim 15, wherein the biological sample is obtained from, part of, or all of a subject, and whereby if myeloma tumor cells are detected or imaged, the subject is diagnosed with multiple myeloma.

* * * * *